United States Patent
Takahashi et al.

(10) Patent No.: US 9,360,492 B2
(45) Date of Patent: Jun. 7, 2016

(54) AUTOMATIC ANALYZER FOR BIOLOGICAL SAMPLES

(75) Inventors: Katsuaki Takahashi, Hitachinaka (JP);
Taku Sakazume, Hitachinaka (JP);
Yukinori Sakashita, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/698,736

(22) PCT Filed: May 18, 2011

(86) PCT No.: PCT/JP2011/002747
§ 371 (c)(1),
(2), (4) Date: Dec. 6, 2012

(87) PCT Pub. No.: WO2011/145337
PCT Pub. Date: Nov. 24, 2011

(65) Prior Publication Data
US 2013/0108508 A1    May 2, 2013

(30) Foreign Application Priority Data

May 20, 2010    (JP) ................................. 2010-115886

(51) Int. Cl.
*G01N 35/10*    (2006.01)
*G01N 35/02*    (2006.01)
*G01N 35/00*    (2006.01)

(52) U.S. Cl.
CPC ........ *G01N 35/1065* (2013.01); *G01N 35/0095* (2013.01); *G01N 35/025* (2013.01); *G01N 2035/0094* (2013.01)

(58) Field of Classification Search
USPC ..................................................... 422/62–67
See application file for complete search history.

(56) References Cited

U.S. PATENT DOCUMENTS

| | | | | |
|---|---|---|---|---|
| 4,276,051 A | * | 6/1981 | Ginsberg et al. | 436/47 |
| 4,595,562 A | * | 6/1986 | Liston et al. | 422/65 |
| 5,352,612 A | * | 10/1994 | Huber et al. | 436/47 |
| 5,422,075 A | * | 6/1995 | Saito et al. | 422/52 |
| 5,985,672 A | * | 11/1999 | Kegelman | G01N 35/0098 422/64 |
| 2002/0064881 A1 | * | 5/2002 | Devlin et al. | 436/43 |
| 2002/0122745 A1 | * | 9/2002 | Takase et al. | 422/63 |
| 2003/0129095 A1 | * | 7/2003 | Farina et al. | 422/102 |
| 2007/0172390 A1 | * | 7/2007 | Ootani et al. | 422/64 |
| 2007/0248490 A1 | * | 10/2007 | Matsuo et al. | 422/64 |
| 2007/0253866 A1 | * | 11/2007 | Rousseau | 422/64 |
| 2008/0014118 A1 | * | 1/2008 | Kitagawa | G01N 35/00663 422/64 |

(Continued)

FOREIGN PATENT DOCUMENTS

| | | |
|---|---|---|
| JP | 03-262970 A | 11/1991 |
| JP | 08-313538 A | 11/1996 |
| JP | 2007-271411 A | 10/2007 |

*Primary Examiner* — Jill Warden
*Assistant Examiner* — Benjamin Whatley
(74) *Attorney, Agent, or Firm* — Mattingly & Malur, PC

(57) ABSTRACT

The automatic analyzer includes: a disk having a plurality of holding sections for holding a plurality of containers on the circumference of the disk or on a closed loop that rotationally moves, the disk adapted to move the plurality of containers; a reagent dispensing mechanism for dispensing a reagent into the container on the disk; and a sample dispensing mechanism for dispensing a sample into the container on the disk. The automatic analyzer also includes a container transfer mechanism for mounting the container in the holding sections on the disk. The container transfer mechanism is driven in such a manner that the container can be mounted in the plurality of holding sections on the disk.

11 Claims, 12 Drawing Sheets

(56) References Cited

U.S. PATENT DOCUMENTS

| | | | |
|---|---|---|---|
| 2008/0019868 A1* | 1/2008 | Okumoto et al. ............... 422/63 |
| 2008/0020481 A1* | 1/2008 | Yamamoto ........... G01N 35/025 |
| | | 436/164 |
| 2008/0318323 A1* | 12/2008 | Shintani ................ B01L 3/5082 |
| | | 436/47 |
| 2009/0191094 A1* | 7/2009 | Kayahara ................ G01N 35/04 |
| | | 422/64 |
| 2009/0308183 A1* | 12/2009 | Cohen ................ G01N 35/0092 |
| | | 73/864.21 |
| 2010/0104478 A1* | 4/2010 | Kondou ........................ 422/100 |
| 2011/0053277 A1* | 3/2011 | Yamato .............. G01N 35/1002 |
| | | 436/43 |

* cited by examiner

FIG. 4 − 1
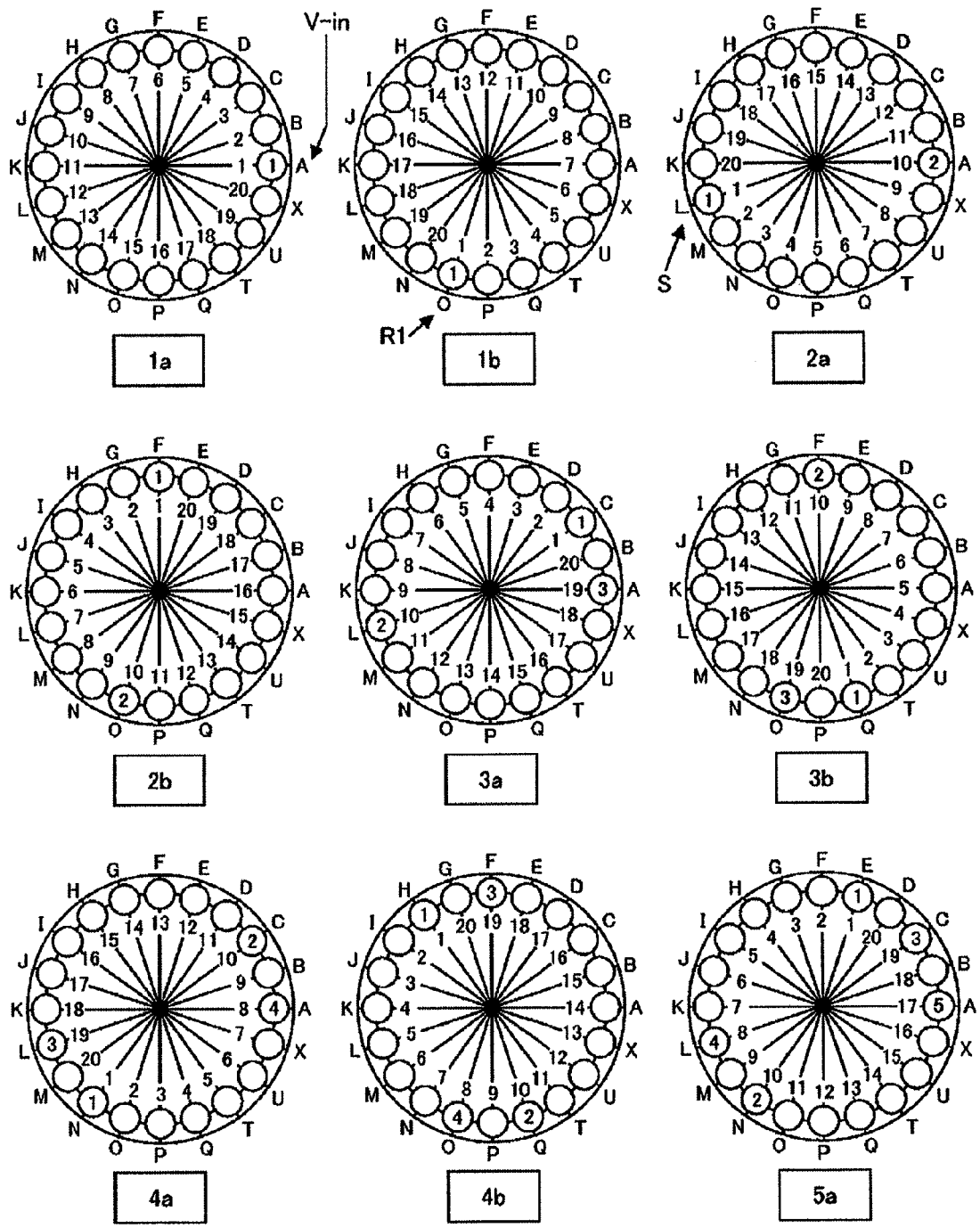

FIG. 4 – 2
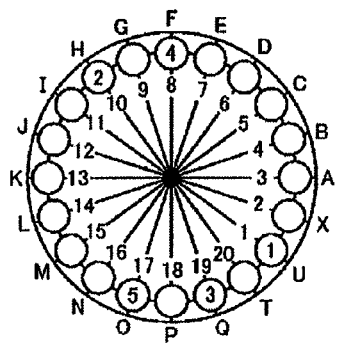
5b
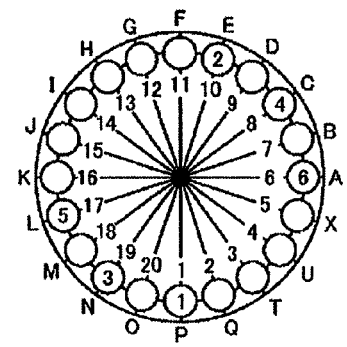
6a
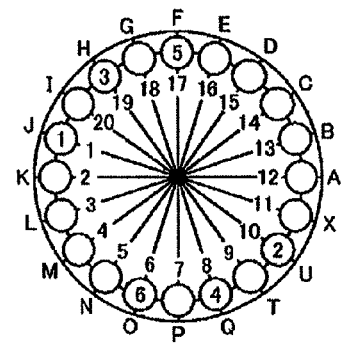
6b
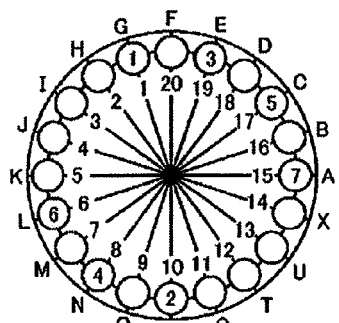
7a
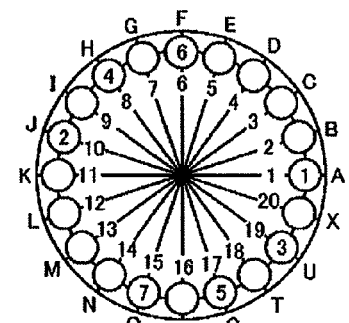
7b
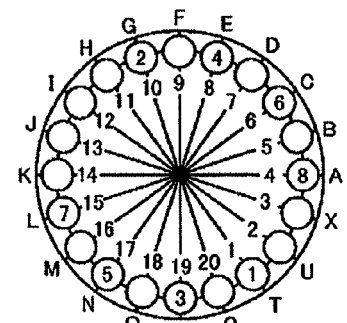
8a
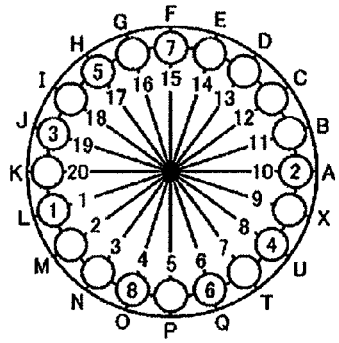
8b
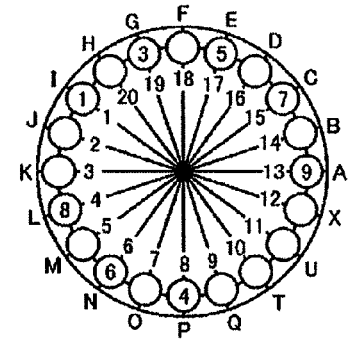
9a
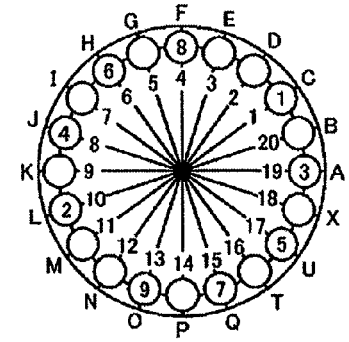
9b

FIG. 4 - 3
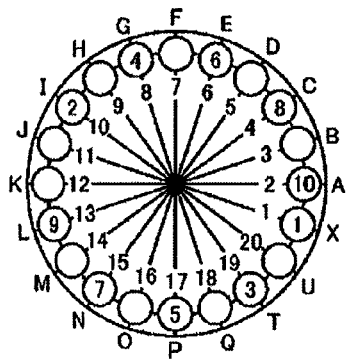
10a
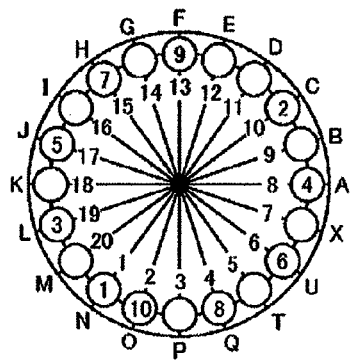
10b
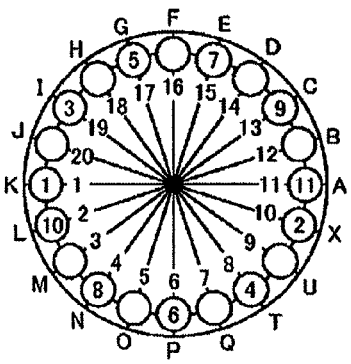
11a
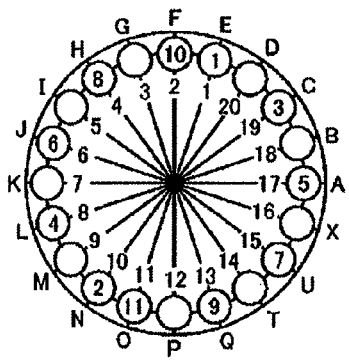
11b
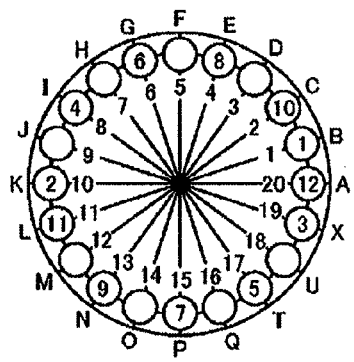
12a
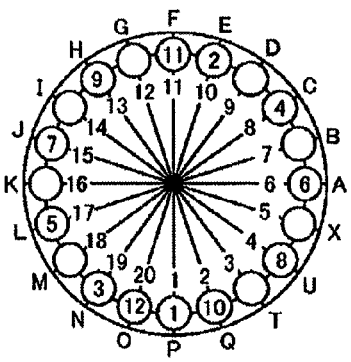
12b
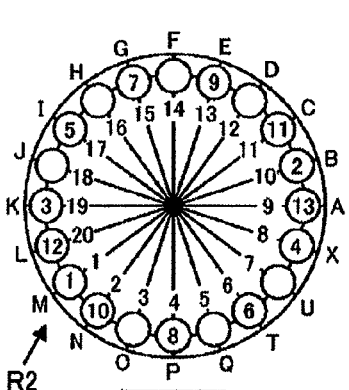
13a
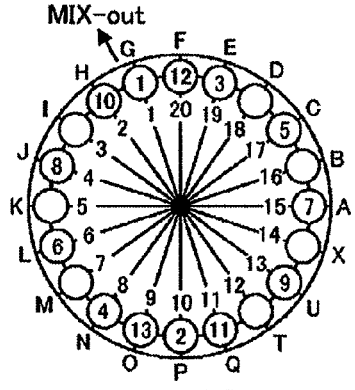
13b
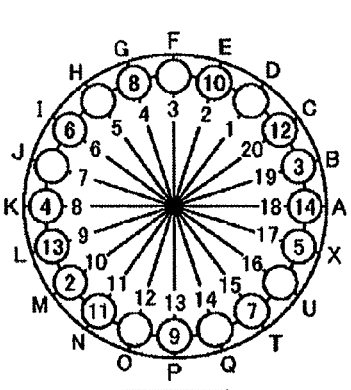
14a

FIG. 4 − 4
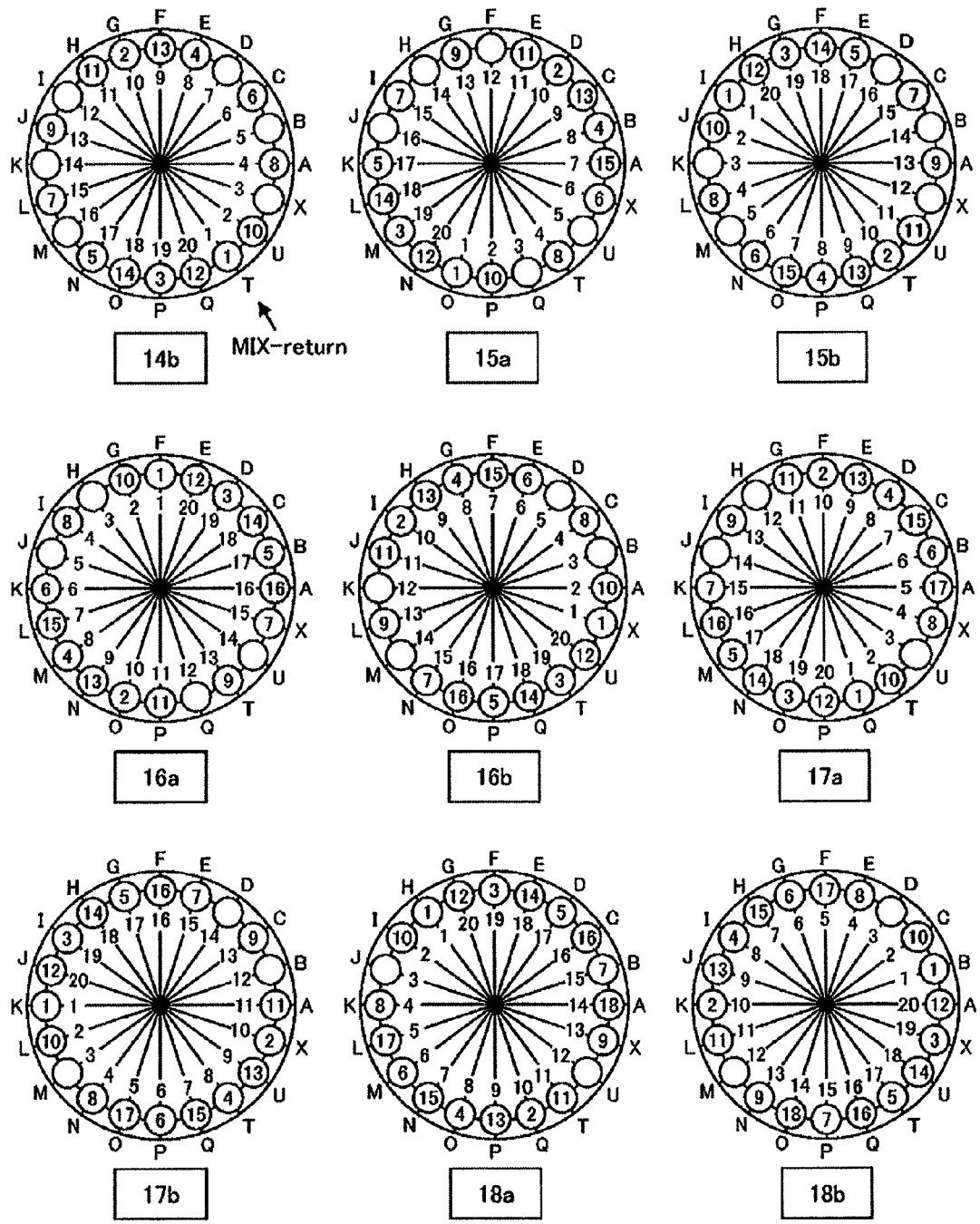

FIG. 4 - 5
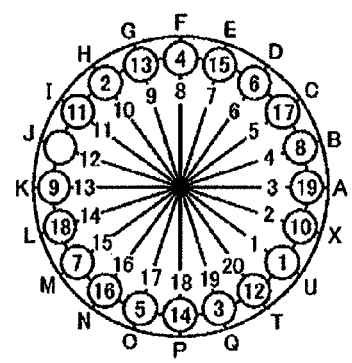
19a
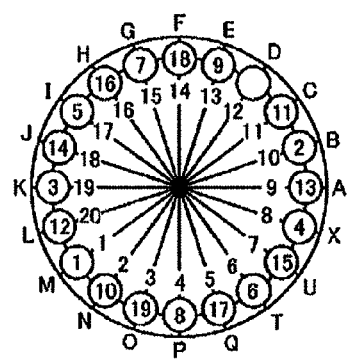
19b
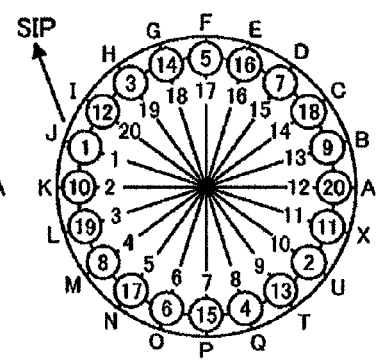
20a
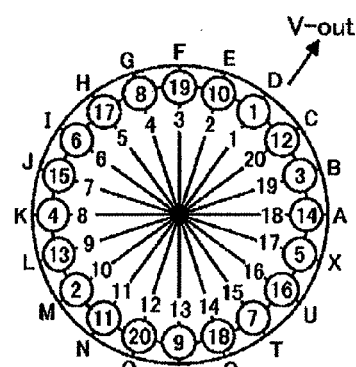
20b
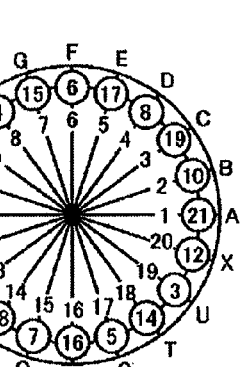
21a

FIG. 5 − 1
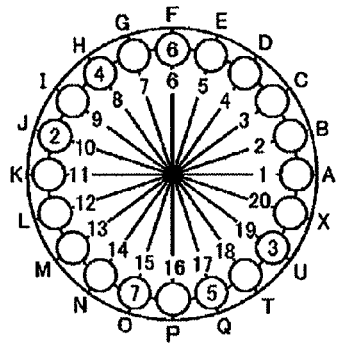
7b
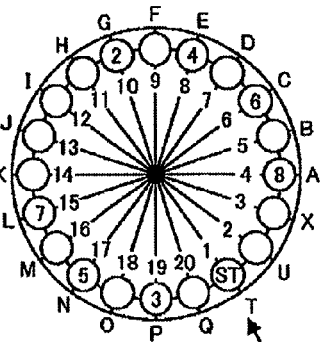
8a
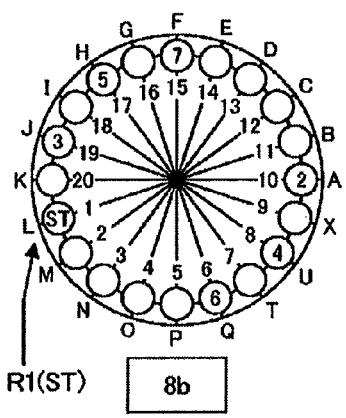
8b
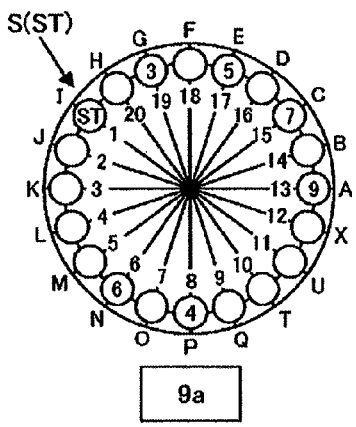
9a
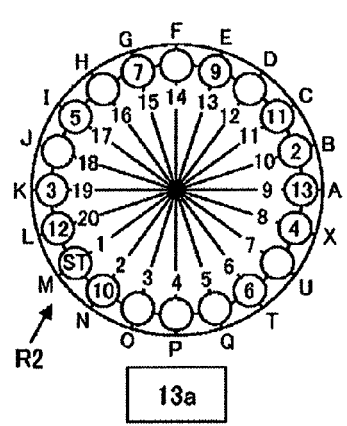
13a
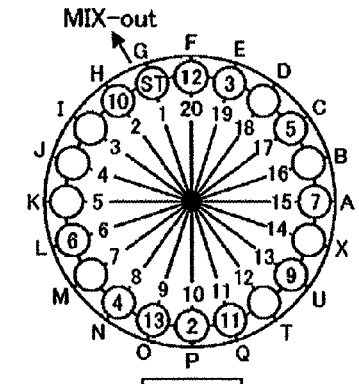
13b
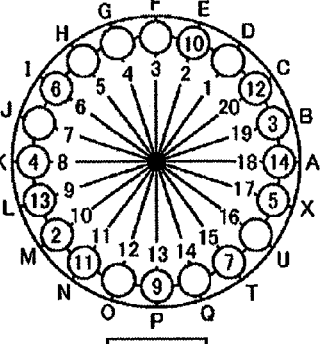
14a

AUTOMATIC ANALYZER FOR BIOLOGICAL SAMPLES

TECHNICAL FIELD

The present invention relates to an automatic analyzer, and more particularly to a technique for shortening or lengthening the reaction time between a sample and a reagent in an automatic analyzer which dispenses and analyzes a biological sample.

BACKGROUND ART

The automatic analyzer is an apparatus for mixing a biological sample and a reagent in a reaction container to react with each other, irradiating a reaction solution with light after the lapse of the predetermined reaction time, and calculating the concentration of a specific component contained in the biological sample from the absorbance of the light which has passed through the reaction solution.

In recent years, automatic analyzers have been forced to handle various kinds of inspection items. Specifically, there is an inspection item on which a correct measurement cannot be made unless the reaction takes place over a longer period of time, or there is an inspection item for which an urgent measurement is necessary and thereby it is necessary for the inspection to be performed with a shorter time of reaction.

As a solution to handle various kinds of inspections items, there is disclosed an automatic analyzer in which a stopping position of a reaction disk is irregularly changed on occasions (Patent Document 1).

PRIOR ART LITERATURE

Patent Documents

Patent Document 1: JP-8-313538-A

SUMMARY OF THE INVENTION

Problems to be Solved by the Invention

However, the method in which the stopping position of the reaction disk is irregularly changed on occasions disclosed in Patent Document 1 cannot avoid a decrease in processing ability. The reason is as follows. When the reaction disk stops, the automatic analyzer concurrently performs the operation of dispensing a reagent/sample, the operation of stirring a solution in a reaction container, the operation of supplying/returning the reaction container and the operation of cleaning the reaction container. However, if the stopping position of the reaction disk becomes irregular only when a certain operation is performed, the irregularity may cause hindrances to the other concurrent parallel operations. Meanwhile, in order not to irregularly change the stopping position of the reaction disk on occasions, the automatic analyzer is forced to provide a large number of idle cycles so as to avoid the interference of the operations. Providing a large number of idle cycles causes the processing ability to decrease remarkably, which may result in a decrease in processing ability to one tenth.

The present invention has been made taking the abovementioned problem into consideration, and an object of the present invention is to provide an automatic analyzer, wherein the processing ability hardly decreases even when a plurality of analyses, each of which requires the different reaction time, exist in parallel.

Means for Solving the Problems

In order to solve the abovementioned problem, the present invention provides the following automatic analyzer.

An analyzer comprises: a disk having a plurality of holding sections for holding a plurality of containers on the circumference of the disk or on a closed loop that rotationally moves, the disk adapted to move the plurality of containers; a reagent dispensing mechanism for dispensing a reagent into the container on the disk; and a sample dispensing mechanism for dispensing a sample into the container on the disk. The analyzer includes a container transfer mechanism for mounting the container in the holding sections on the disk. The container transfer mechanism is driven in such a manner that the container can be mounted in the plurality of holding sections on the disk.

Effects of the Invention

According to the present invention, items, each of which is provided with the reaction time that is shortened or lengthened, can be concurrently analyzed, and the decrease in processing ability can be minimized to the utmost.

BRIEF DESCRIPTION OF THE DRAWINGS

FIG. 4-1 shows diagrams which constitute an animation illustrating a reference operation sequence;

FIG. 4-2 are diagrams which constitute an animation illustrating a reference operation sequence;

FIG. 4-3 shows diagrams which constitute an animation illustrating a reference operation sequence;

FIG. 4-4 shows diagrams which constitute an animation illustrating a reference operation sequence;

FIG. 4-5 shows diagrams which constitute an animation illustrating a reference operation sequence;

FIG. 5-1 shows diagrams which constitute an animation illustrating a sequence executed when an urgent analysis is requested as an interruption;

FIG. 5-2 shows diagrams which constitute an animation illustrating a sequence executed when an urgent analysis is requested as an interruption;

MODES FOR CARRYING OUT THE INVENTION

The invention will be summarized before embodiments are described.

With respect to the conventional automatic analyzers, a position at which an arm of a reagent dispensing mechanism is capable of accessing a reaction disk is usually fixed (one position, or two positions on the circular arc through which the arm passes). In addition, reaction containers are mounted on the reaction disk from a fixed position.

According to the present invention, by providing an automatic analyzer with a reaction container transfer mechanism, reaction containers can be mounted on a reaction disk from a plurality of positions. Meanwhile, although the reaction container transfer mechanism is capable of accessing the reaction disk from a plurality of positions, the reaction container transfer mechanism is configured not to access an operating range of an arm of a reagent dispensing mechanism. Consequently, by adjusting a position at which the reaction container is mounted, and the timing in which the reaction container is mounted, the reaction time of a reagent can be adjusted without performing the complicated operation and control of the dispensing mechanism. Therefore, a plurality of analyses, each of which requires the different reaction time, can be executed on the same disk.

An automatic analyzer according to the present invention will be described in detail with reference to drawings as below.

Figure 1:
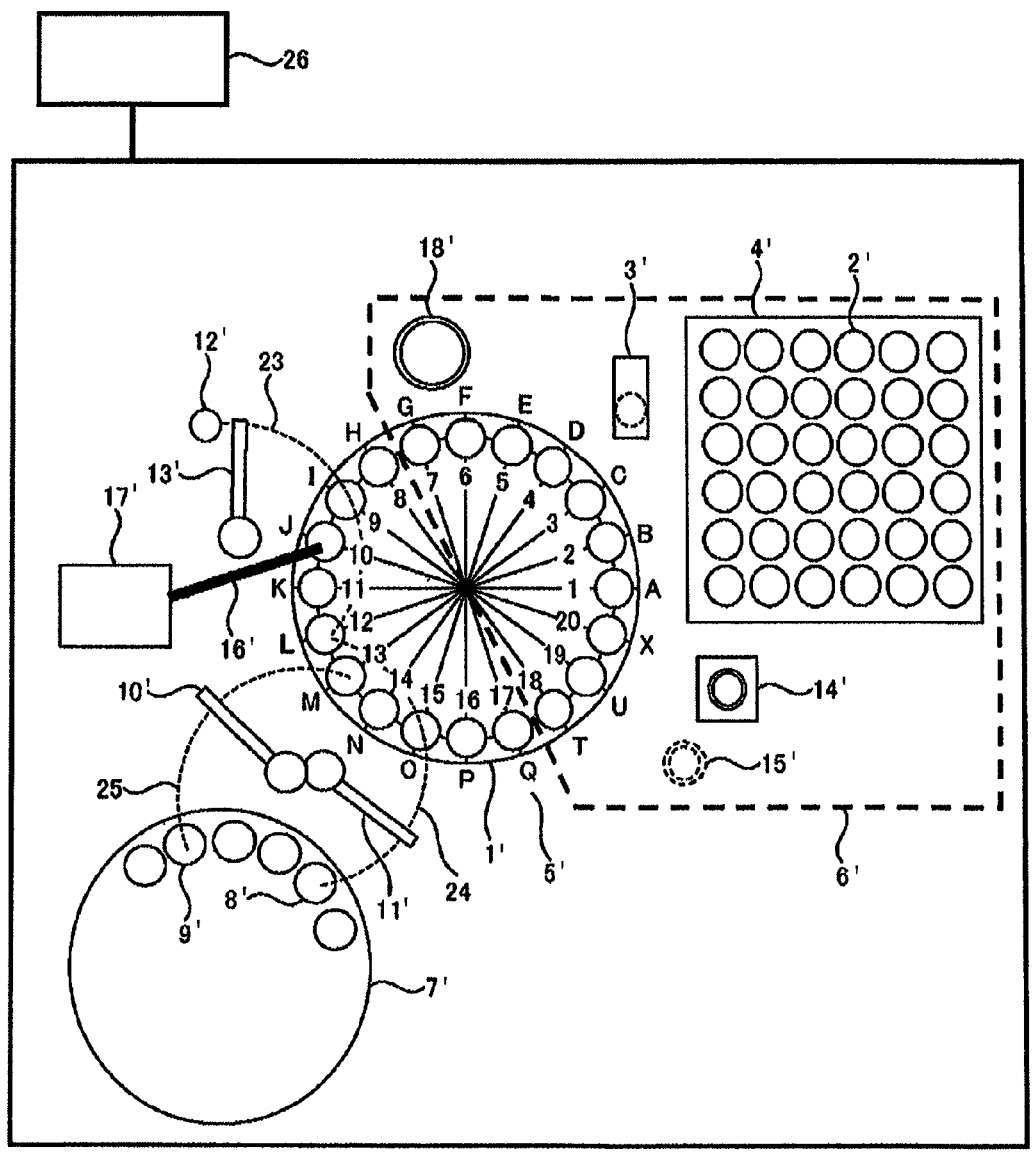
FIG. 1 is a diagram illustrating a layout of each mechanism of an automatic analyzer according to the present invention.

FIG. 1 is a diagram illustrating how mechanism components of the automatic analyzer according to the present invention are arranged.

The automatic analyzer is provided with a reaction disk 1' in which a biological sample reacts with a reagent. The reaction disk 1' is formed with 20 holes as an example, and twenty hole numbers (1 to 20) are assigned to the holes respectively. The reaction disk can be rotated by a reaction disk driving mechanism (not illustrated). When the reaction disk rotates, the hole numbers also rotate therewith.

Further, hole positions when the reaction disk 1' stops are provided with twenty identification numbers (A to X) respectively as rest coordinate positions. The identification numbers (A to X) do not move even when the reaction disk 1' rotates. A reaction container transfer mechanism 3' catches and transfers each of reaction containers 2' that are mounted and arrayed on a magazine 4'. A range within which the reaction container transfer mechanism 3' is capable of transferring and moving each reaction container is limited within a reaction container transfer mechanism movable area 6'. The reaction container transfer mechanism 3' is capable of accessing 36 reaction container positions on the magazine, and the holes at fixed coordinate positions T, U, X, A, B, C, D, E, F, G on the reaction disk 1'. The reaction container transfer mechanism movable area 6' does not overlap the undermentioned reagent dispensing mechanism, and a movable range of a sample dispensing mechanism.

Moreover, the reaction container transfer mechanism 3' is capable of moving to a reaction container stirring mechanism 14', a reaction container holding section 15' and a reaction container disposal outlet 18'.

An arm 11' of a first reagent (R1) dispensing mechanism is arranged in such a manner that the locus 24 of a first reagent probe passes through the rest coordinate positions O and L. Further, an arm 10 of a second reagent (R2) dispensing mechanism is arranged in such a manner that the locus 25 of a second reagent probe passes through the rest coordinate position M. Reagents 8', 9' mounted on the reagent disk 7' can be dispensed into reaction containers on the reaction disk. An arm 13' of a sample (S) dispensing mechanism is arranged in such a manner that the moving locus 23 of a sample probe passes through the rest coordinate positions L and I. A shipper nozzle 16' is arranged at the rest coordinate position J to introduce a reaction solution into a measurement unit 17', and measurement is performed.

A computer 26 controls the reaction disk driving mechanism, the reaction container transfer mechanism 3', the reaction container stirring mechanism 14', the arm 11' of the first reagent (R1) dispensing mechanism, the arm 13' of the sample (S) dispensing mechanism, and the like.

Incidentally, the reaction disk driving mechanism rotates the reaction disk. If the number of the holes is 20, the rotation by 18° (=360°/20) means that the reaction disk moves by 1 pitch.

Next, an access position at which an access is made to a reaction container on the reaction disk 1' will be described in summary with reference to FIG. 2.

In the case of normal analysis, an access is made in the following sequence:

(1) At the rest coordinate position A, a reaction container is supplied (V-in);

(2) At the rest coordinate position O, a first reagent R1 is dispensed (R1);

(3) At the rest coordinate position L, a sample S is dispensed (S);

(4) At the rest coordinate position M, a second reagent R2 is dispensed (R2);

(5) At the rest coordinate position G, the reaction container transfer mechanism 3' takes out the reaction container, and then transfers the reaction container to the reaction container stirring mechanism 14' shown in FIG. 1 (MIX-out);

(6) At the rest coordinate position T, the reaction container after stirring is returned by the reaction container transfer mechanism (MIX-return);

(7) At the rest coordinate position J, the shipper nozzle is inserted to suck a reaction solution, thereby measuring the concentration of the reaction solution, and the like (SIP); and (8) At the rest coordinate position D, the reaction container is disposed of to the reaction container disposal outlet 18' (V-out).

In addition, in the case of urgent analysis (referred to as ST) in which the reaction time is shortened, an access is made in the following sequence (among the abovementioned steps (1) to (8), (1), (2), (3) and (6) are changed):

(1)' At the rest coordinate position T, a reaction container for urgent analysis is supplied (V-in(ST));

(2)' At the rest coordinate position L, a first reagent for urgent analysis is dispensed (R1(ST));

(3)' At the rest coordinate position I, a sample S for urgent analysis is dispensed (S(ST));

(4) At the rest coordinate position M, the second reagent R2 is dispensed (R2);

(5) At the rest coordinate position G, the reaction container transfer mechanism 3' takes out the reaction container, and then transfers the reaction container to the reaction container stirring mechanism 14' shown in FIG. 1 (MIX-out);

(6)' At the rest coordinate position U, the reaction container for urgent analysis after stirring is returned by the reaction container transfer mechanism 3' (MIX-return(ST));

(7) At the rest coordinate position J, the shipper nozzle is inserted to suck a reaction solution, thereby measuring the concentration of the reaction solution, and the like (SIP); and (8) At the rest coordinate position D, the reaction container is disposed of to the reaction container disposal outlet 18 (V-out).

Figure 2:
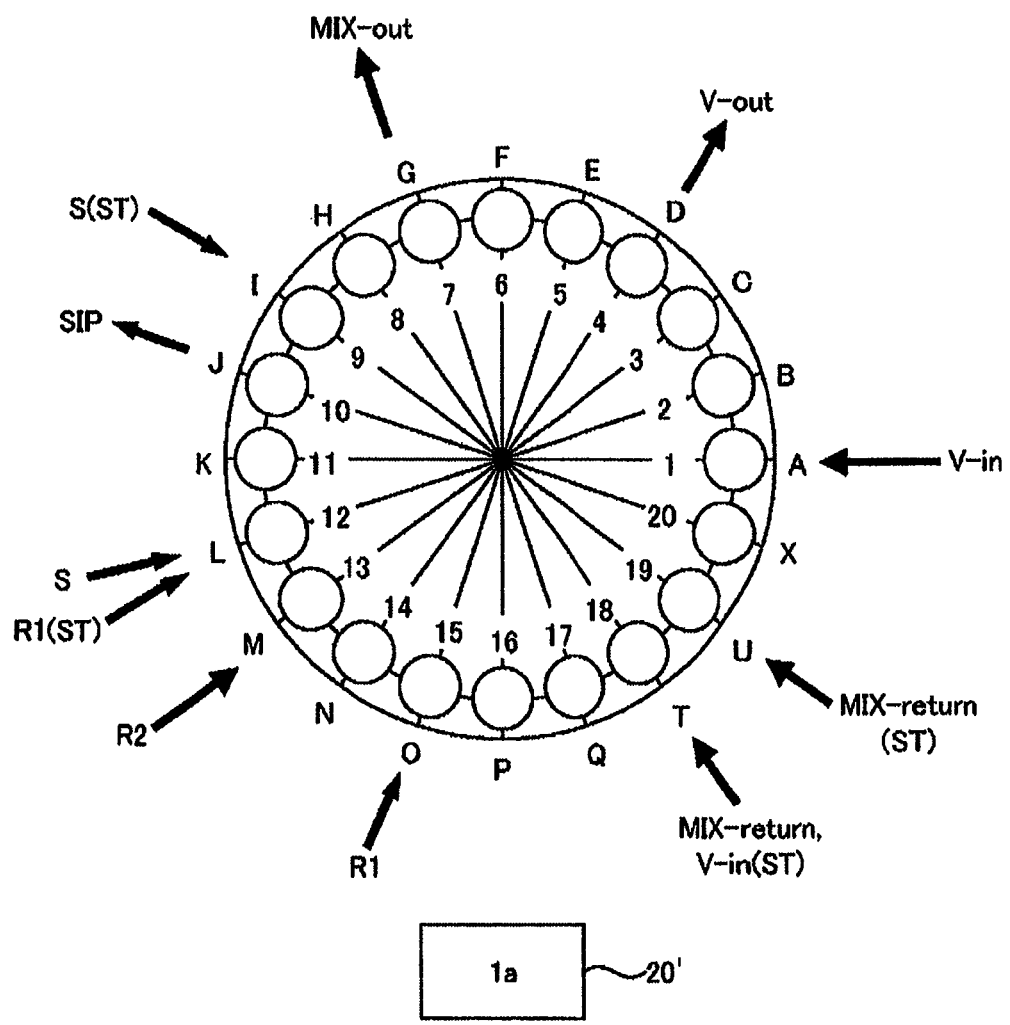
FIG. 2 is a diagram illustrating access positions for a function of supplying/returning a reaction container to/from a reaction disk, a function of dispensing a reagent and a sample, and a stirring function.
Figure 5:
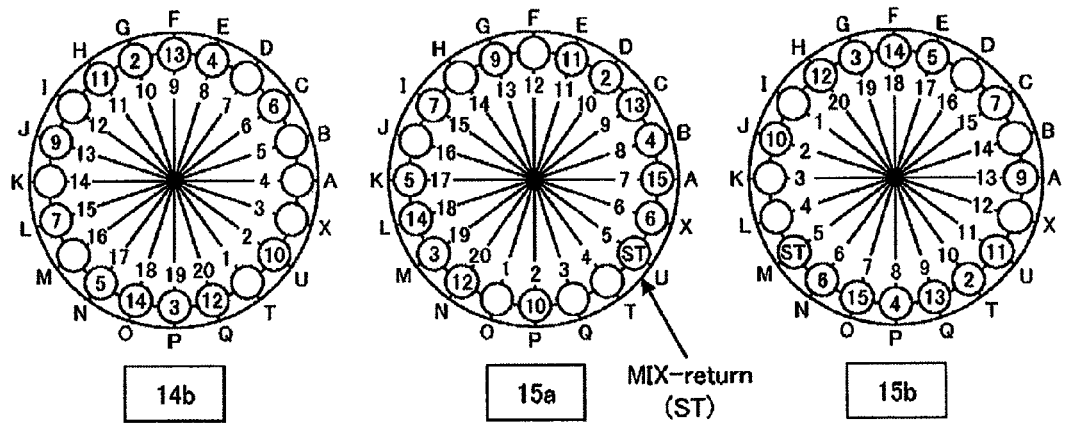
Figure 2:
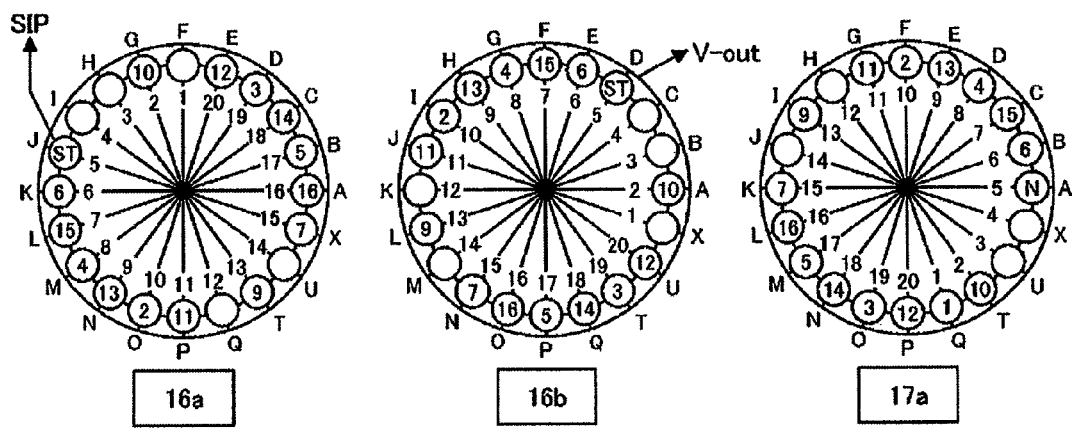

Characters shown in a display box 20' of FIG. 2 indicate a cycle number and a stop period (a or b) used when the operation is illustrated with animations after FIGS. 4-1 to 4-5.

A time sequence for performing processing will be described.

Figure 3:
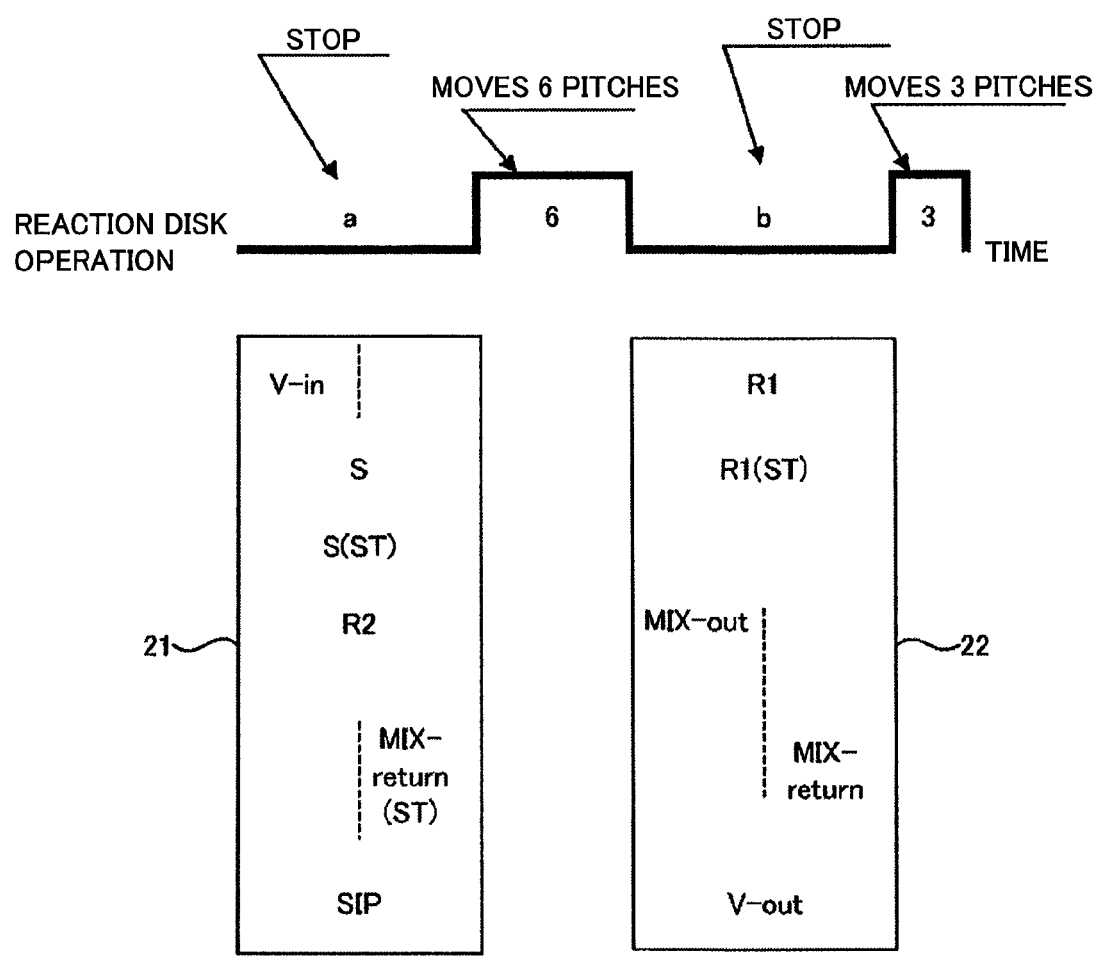
FIG. 3 is a diagram illustrating a time chart of each mechanism corresponding to the move operation and stop operation of a reaction disk.

FIG. 3 illustrates a basic time sequence.

A time sequence for normal analysis is performed as follows.

I. The reaction disk 1 stops during a stop period a.

During the stop period a, the following operation is performed:

(1) At the rest coordinate position A, a reaction container is supplied (V-in);

(3) At the rest coordinate position L, the sample S is dispensed (S);

(4) At the rest coordinate position M, the second reagent R2 is dispensed (R2); and (7) At the rest coordinate position J, the shipper nozzle is inserted to suck a reaction solution, thereby measuring the concentration of the reaction solution, and the like (SIP).

When an urgent analysis is requested, the following steps are also concurrently performed:

(1)' At the rest coordinate position T, a reaction container for urgent analysis is supplied (V-in(ST)); and (3)' At the rest coordinate position I, a sample S for urgent analysis is dispensed (S(ST)).

II. The reaction disk moving mechanism moves the reaction disk 1' by 6 pitches.

III. The reaction disk 1 stops during a stop period b.

During the stop period b, the following operation is performed:

(2) At the rest coordinate position O, the first reagent R1 is dispensed (R1);

(5) At the rest coordinate position G, the reaction container transfer mechanism 3' takes out the reaction container, and then transfers the reaction container to the reaction container stirring mechanism 14' shown in FIG. 1 (MIX-out);

(6) At the rest coordinate position T, the reaction container after stirring is returned by the reaction container transfer mechanism (MIX-return); and (8) At the rest coordinate position D, the reaction container is disposed of to the reaction container disposal outlet 18' (V-out).

When an urgent analysis is requested, the following steps are also concurrently performed:

(2)' At the rest coordinate position L, a first reagent for urgent analysis is dispensed (R1(ST)); and (6)' At the rest coordinate position U, the reaction container for urgent analysis after stirring is returned by the reaction container transfer mechanism (MIX-return(ST)).

IV. The reaction disk moving mechanism moves the reaction disk 1' by 3 pitches.

The operation of I to IV is repeated thereafter (I to IV constitute one cycle). The reaction disk 1' moves by 9 pitches in one cycle. However, the number of pitches the reaction disk 1' moves in one cycle, which is 9, and the number of holes of the reaction disk 1', which is 20, are coprime to each other, and therefore all of 20 reaction containers on the reaction disk 1' can be used by repeating moving the reaction disk 1' by 9 pitches. The number of holes and the number of pitches the reaction disk 1' moves in one cycle are not limited to the above numbers. All of the reaction containers on the reaction disk 1' can be used so long as the number of pitches the reaction disk 1' moves in one cycle and the number of holes of the reaction disk 1' are coprime to each other.

Next, the operation will be described with animations with reference to FIGS. 4-1 to 4-5.

Here, the abovementioned time sequence I to IV (in other words, na→nb→(n+1)a, n=1, 2, . . . ) is called 1 cycle, and na→nb and nb→(n+1)a are each called 0.5 cycle.

FIGS. 4-1 to 4-5 each illustrate an analysis of an item based on the standard reaction time (18.5 cycles from R1 dispensing to SIP measurement). Although 1a, 1b, 2a, 2b . . . are shown in the display box 20', 1a indicates a state of the stop period a in the first cycle (a state of I in the sequence), 1b indicates a state of the stop period b in the first cycle (a state of III in the sequence), 2a indicates a state of the stop period a in the second cycle (a state of I in the sequence), and 2b indicates a state of the stop period b in the second cycle (a state of III in the sequence).

The number xx shown in each circle of the reaction disk indicates that a reaction container is filled with a reaction solution of the xx-th test. The reaction disk 1' rotates clockwise by 6 pitches (a state of II in the sequence) during a→b in each cycle (for example, 1a→1b), and rotates clockwise by 3 pitches (a state of IV in the sequence) during b in each cycle→a in the next cycle (for example, 1b→2a). The same operation is repeated thereafter.

| | |
|---|---|
| 1a | The hole number 1 stops at the rest coordinate position A, and a reaction container (number 1) is supplied (V-in). |
| 1b | The hole number 1 stops at the rest coordinate position O, and the first reagent R1 is dispensed into the reaction container (number 1). |
| 2a | The hole number 1 stops at the rest coordinate position L, and the sample S is dispensed into the reaction container (number 1). The hole number 10 stops at the rest coordinate position A, and a reaction container (number 2) is supplied (V-in). |
| 2b | The hole number 1 stops at the rest coordinate position F. The hole number 10 stops at the rest coordinate position O, and the first reagent R1 is dispensed into the reaction container (number 2). |
| 3a | The hole number 1 stops at the rest coordinate position C. The hole number 10 stops at the rest coordinate position L, and the sample S is dispensed into the reaction container (number 2). The hole number 19 stops at the rest coordinate position A, and a reaction container (number 3) is supplied (V-in). |
| 3b | The hole number 1 stops at the rest coordinate position Q. The hole number 10 stops at the rest coordinate position F. The hole number 19 stops at the rest coordinate position O, and the first reagent R1 is dispensed into the reaction container (number 3). |

In the description thereafter, only the reaction container (number 1) in the hole number 1 will be described, and for the other hole numbers, only the numbers will be shown in the figures.

The other reaction containers also follow the same sequence with the order thereof sequentially shifted by one cycle.

| | |
|---|---|
| . . . | . . . |
| 13a | The hole number 1 stops at the rest coordinate position M, and the second reagent R2 is dispensed into the reaction container (number 1). |
| 13b | The hole number 1 stops at the rest coordinate position G, and the reaction container transfer mechanism takes out the reaction container (number 1), and transfers the reaction container (number 1) to the stirring mechanism, and stirring is performed. |
| 14a | Although the hole number 1 stops at the rest coordinate position D, the hole having the hole number 1 is kept empty. Stirring is being continued. |
| 14b | The hole number 1 stops at the rest coordinate position T, and the reaction container transfer mechanism returns the reaction container (number 1) from the stirring mechanism to the hole number 1. |
| . . . | . . . |
| 20a | The hole number 1 stops at the rest coordinate position J, the shipper nozzle 16 is inserted into the reaction container (number 1) to suck a reaction solution into the measurement unit 17, and the concentration of the reaction solution, and the like, are measured. |

-continued

| 20b | The hole number 1 stops at the rest coordinate position D, and the reaction container transfer mechanism takes out the reaction container (number 1), and disposes of the reaction container (number 1) to the disposal outlet. |
| --- | --- |
| 21a (=1a) | The hole number 1 stops at the rest coordinate position A, and a reaction container (number 21) is supplied (V-in). |
| ... | ... |

Figure 6:
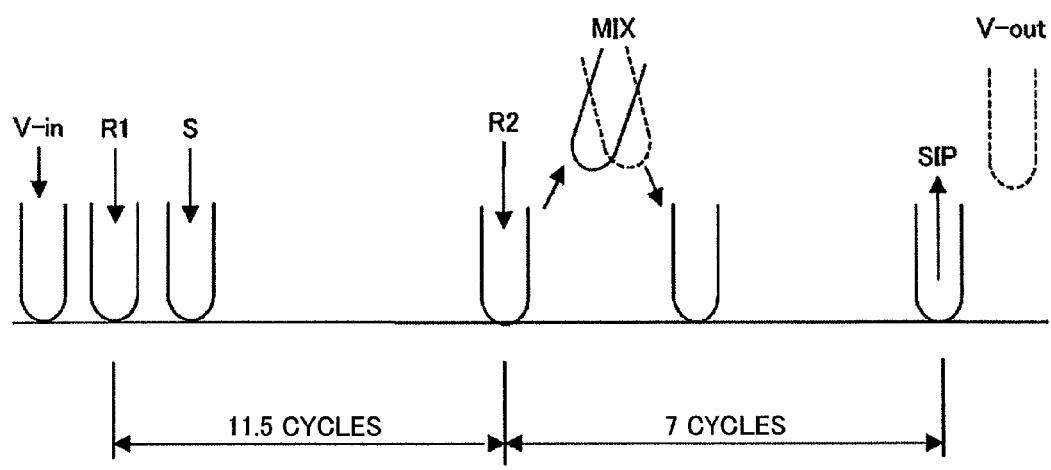
FIG. 6 is a diagram which summarizes a reaction process in a reference operation sequence.

The sequence with the standard reaction time was described as above. The sequence is summarized as shown in FIG. 6. The operation from R1 dispensing (1b) to SIP measurement (20a) requires 18.5 cycles, which is the normal reaction time.

Next, an interruption sequence which is caused by an urgent measurement (the reaction time is short) will be described with reference to FIGS. 5-1 and 5-2.

The reaction time of the urgent measurement is short, and is uniformly determined. On receipt of an urgent measurement request, the computer 26 checks whether or not the reaction disk 1' has an empty hole thereon. When the reaction disk 1' has an empty hole thereon, the computer subsequently checks whether or not the operation of, for example, the dispensing mechanism interferes with the reserved operation from the viewpoint of the timing. Moreover, the computer further checks whether or not a hole at a position at which the reaction container is to be returned after stirring is also empty. As the result of such checks, when it is determined that no problem will arise in the case of an interruption, the interruption is started. An interruption sequence will be described as below.

| 7a | It is assumed that the operation has been performed up to 7b with the hole number 1 kept empty and unused. |
| --- | --- |
| 7b | The hole number 1 stays at the rest coordinate position T, and a reaction container (ST) is supplied (V-in(ST)). |
| 8a | The hole number 1 stays at the rest coordinate position L, and the first reagent is dispensed (R1(ST)). |
| 8b | The hole number 1 stays at the rest coordinate position I, and a sample is dispensed (S(ST)). |
| ... | ... |
| 13a | The hole number 1 stays at the rest coordinate position M, and the second reagent is dispensed (R2). |
| 13b | The hole number 1 stays at the rest coordinate position G, the reaction container transfer mechanism takes out the reaction container (ST), and transfers the reaction container (ST) to the stirring mechanism, and stirring is performed. |
| ... | ... |
| 15a | The hole number 5 stops at the rest coordinate position U with the hole having the hole number 5 kept empty, and the reaction container transfer mechanism returns the reaction container (ST) from the stirring mechanism to the hole number 5. |
| 15b | The hole number 5 stays at the rest coordinate position M. |
| 16a | The hole number 5 stops at the rest coordinate position J, the shipper nozzle 16 is inserted into the reaction container (ST) to suck a reaction solution into the measurement unit 17, and the concentration of the reaction solution, and the like, are measured. |
| 16b | The hole number 5 stops at the rest coordinate position D, and the reaction container transfer mechanism takes out the reaction container (ST), and disposes of the reaction container (ST) to the disposal outlet. |
| 17a | The hole number 5 stops at the rest coordinate position A, and a reaction container (number N) is supplied (V-in). |

Figure 7:
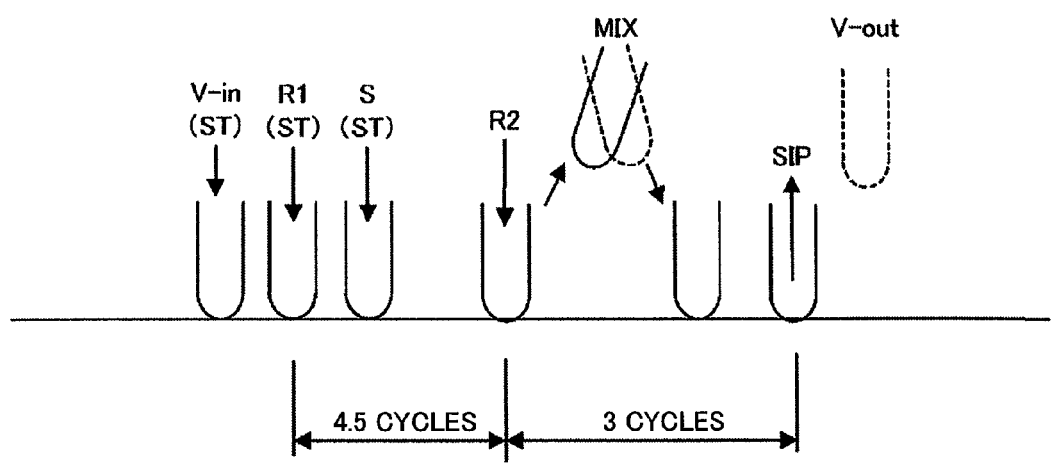
FIG. 7 is a diagram which summarizes a reaction process in an urgent analysis sequence (example 1)

FIG. 7 illustrates the summary of the abovementioned interruption caused by the urgent measurement item, and reveals that the operation from R1 dispensing to SIP measurement requires 7.5 cycles which is the short reaction time.

In this example of the urgent interruption, the dispensing and stirring of R2 are performed in the same timing as the usual one, the first half (from the first reagent dispensing (R1(ST)) to the second reagent dispensing (R2)) is shortened to 4.5 cycles, and the latter half (from the second reagent dispensing (R2) to sucking (SIP)) is shortened to 3 cycles.

Figure 8:
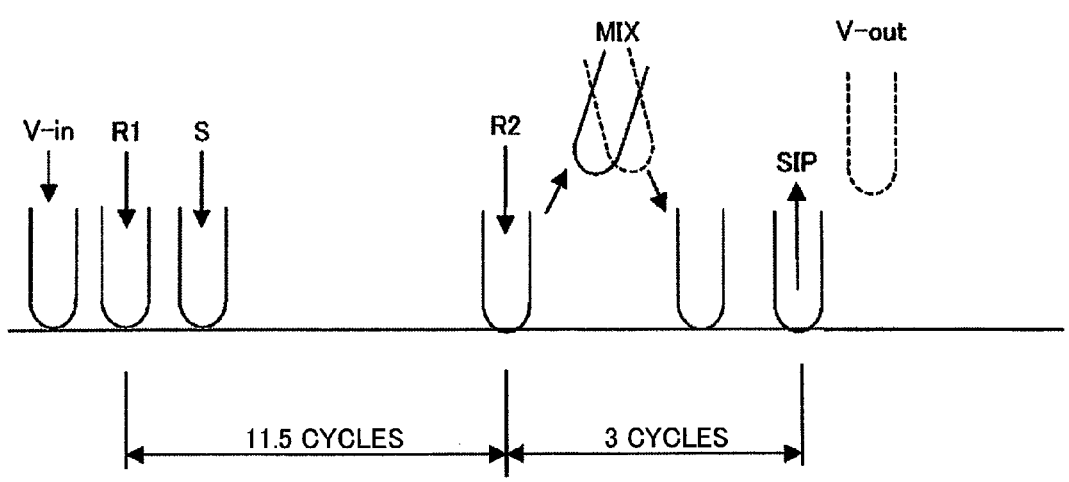
FIG. 8 is a diagram which summarizes a reaction process in an urgent analysis sequence (example 2).

FIG. 8 illustrates an example in which only the latter half is shortened to 3 cycles. In this case, as described above, the automatic analyzer has only to change a position at which the reaction container transfer mechanism returns the reaction container after stirring of the reaction container.

Incidentally, in order to enable the automatic analyzer to handle an interruption more easily, providing an idle cycle once every several cycles makes it possible to shorten the wait time.

Further, the use of the reaction container holding section 15' (FIG. 1) makes it possible to configure various kinds of reaction sequences. The reaction container is not immediately returned from the reaction container stirring mechanism 14', but is temporarily mounted in the reaction container holding section 15'. This is because the reaction container stirring mechanism 14' cannot continuously hold the reaction container since the next reaction container will arrive at the reaction container stirring mechanism 14'.

Various kinds of reaction sequences can be executed by returning the reaction container mounted in the reaction container holding section 15' to the target hole instead of supplying a new reaction container thereto in the timing of V-in. When a reaction sequence of each item is made and executed, if a target hole does not enter the reaction container transfer mechanism movable area 6' (the target hole is outside the area) even in the timing in which a reaction container should be returned to the reaction disk, the automatic analyzer has only to temporarily mount the reaction container at a waiting position, and to return the reaction container when the target hole enters the area. A variety of reaction sequences can be made by using this idling method. If two or more reaction container holding sections 15' are provided, a larger variety of reaction sequences can be made.

As another embodiment, how to lengthen the reaction time will be described. With respect to 14b in FIGS. 4-1 to 4-5, MIX-return is returned to the rest coordinate position T. However, if MIX-return is returned to the rest coordinate position U, the time can be lengthened by 9 cycles. As a matter of course, it is necessary to keep the hole having the hole number 2 unused and empty by means of scheduling.

In the abovementioned embodiments, when the second reagent dispensing (R2) is performed, the dispensing position in the case of the normal sample is the same as that in the case of the urgent sample. For example, the dispensing position of R1 differs from that of R1(ST). However, in order to make the dispensing positions uniform, only when R1(ST) dispensing is performed, instead of rotating the reaction disk by 6 pitches, the reaction disk is rotated by 3 pitches, is then temporarily stopped to perform only the R1(ST) dispensing operation, and is further moved by 3 pitches immediately thereafter. This makes it possible to suppress the reduction in processing ability, and to concurrently execute analyses each requiring the different reaction time.

In addition, there is also a case where a proper hole which allows a reaction container for urgent analysis to be mounted therein is not empty on the reaction disk 1'. However, also in this case, the reaction disk 1 can also be temporarily stopped at a dispensing position in a similar manner to perform reagent dispensing.

DESCRIPTION OF REFERENCE NUMERALS

1' Reaction disk
2' Reaction container

3' Reaction container transfer mechanism
4' Magazine
6' Reaction container transfer mechanism movable area
7' Reagent disk
8' First reagent
9' Second reagent
10' Arm of the second reagent dispensing mechanism
11' Arm of the first reagent dispensing mechanism
12' Sample S
13' Arm of the sample (S) dispensing mechanism
14' Reaction container stirring mechanism
15' Reaction container holding section
16' Shipper nozzle
17' Measurement unit
18' Reaction container disposal outlet
20' Display box
21 Job of parallel operational processing during the stop period a
22 Job of parallel operation processing during the stop period b
23 Driving range of the arm of the sample (S) dispensing mechanism
24 Driving range of the arm of the first reagent dispensing mechanism
25 Driving range of the arm of the second reagent dispensing mechanism
26 Computer

The invention claimed is:

1. An analyzer comprising:
a disk, driven by a driving mechanism, having a plurality of holding sections on a circumference of the disk for removably holding a plurality of containers, the driving mechanism is configured to move the plurality of containers held in the holding sections to a plurality of rest coordinate positions, which are each fixed at different angles around a circumference of the disk and do not move with the disk, and the holding sections are arranged exclusively in a single row on the circumference disk, the plurality of rest coordinate positions include at least two predetermined rest coordinate positions at which a holding section accepts a new container;
a reagent dispenser configured to dispense a reagent into the containers on the disk at one of the plurality of rest coordinate positions;
a sample dispenser configured to dispense a sample into the containers on the disk at another of the plurality of rest coordinate positions;
a measurement unit configured to measure a reaction solution in a container at yet another of the plurality of rest coordinate positions;
a magazine configured to hold a plurality of new containers;
a container transfer mechanism configured to access a plurality of holding sections and to transfer a new container from the magazine to a holding section on the single row that is positioned at any of the at least two predetermined rest coordinate positions at which the holding section accepts a new container;
a stirring mechanism disposed outside of the disk and configured to stir the sample and the reagent in one of the containers; and
a computer connected to each of the driving mechanism, reagent dispenser, sample dispenser, measurement unit, container transfer mechanism, and stirring mechanism, wherein the computer is programmed to:

control the container transfer mechanism to transfer one of the containers between the disk and the stirring mechanism,
control the driving mechanism to rotate the disk according to a sequence during a normal analysis of a first reaction solution having a first reaction time, and to rotate the disk according to the sequence during an interrupt analysis of a second reaction solution having a second reaction time shorter than the first reaction time,
receive a measurement request requesting the interrupt analysis of the second reaction solution having the second reaction time that is shorter than the first reaction time,
determine whether the disk has an empty holding section which defines a state in which a new container can be supplied to a holding section on the single row that is positioned at one of the at least two predetermined rest coordinate positions at which the holding section accepts a new container, and
wherein the computer is programmed to control the container transfer mechanism according to the normal analysis and begin controlling the container transfer mechanism according to the interrupt analysis upon reception of the measurement request, upon the disk being in the state in which a new container can be supplied to a holding section on the single row that is positioned at one of the at least two predetermined rest coordinate positions at which the holding section accepts a new container,
wherein during the normal analysis, the computer is programmed to control the container transfer mechanism to transfer a new container from the magazine to a holding section on the single row that is positioned at one of the at least two predetermined rest coordinate positions at which the holding section accepts a new container, and
wherein during the interrupt analysis, the computer is programmed to control the container transfer mechanism to transfer a new container from the magazine to a holding section on the single row that is positioned at another of the at least two predetermined rest coordinate positions at which the holding section accepts a new container, which is a rest coordinate position different from the rest coordinate position that a holding section is positioned to transfer a new container during the normal analysis.

2. The analyzer according to claim 1,
wherein the container transfer mechanism moves in an area that includes the magazine and the stirring mechanism and does not overlap a driving range of the reagent dispensing mechanism and the driving range of the sample dispensing mechanism.

3. The analyzer according to claim 1, further comprising:
a temporary container holding section that temporarily holds one of the containers which is transferred from the disk, is subjected to treatment, and is transferred to the disk again.

4. The analyzer according to claim 1, further comprising:
a stirring mechanism configured to stir a reaction solution in one of the containers prior to measuring,
wherein the container transfer mechanism transfers one of the containers from one of the holding sections of the disk at a first rest coordinate position to the stirring mechanism.

5. The analyzer according to claim 4,
wherein the stirring mechanism stirs the reaction solution in one of the containers transferred by the container transfer mechanism, and the container transfer mechanism transfers the one of the containers from the stirring mechanism to another one of the holding sections of the disk at a second rest coordinate position.

6. The analyzer according to claim 1, wherein
the plurality of rest coordinate positions include at least two predetermined rest coordinate positions at which a reagent is dispensed into a reaction container held by a holding section,
wherein the plurality of rest coordinate positions include at least two predetermined rest coordinate positions at which a sample is dispensed into a reaction container held by a holding section,
wherein during the normal analysis, the computer is programmed to control the reagent dispenser to dispense a reagent to a container held by a holding section on the single row that is positioned at one of the at least two predetermined rest coordinate positions at which a reagent is dispensed into a reaction container held by a holding section,
wherein during the normal analysis, the computer is programmed to control the sample dispenser to dispense a sample to a container held by a holding section on the single row that is positioned at one of the at least two predetermined rest coordinate positions at which a sample is dispensed into a reaction container held by a holding section,
wherein during the interrupt analysis, the computer is programmed to control the reagent dispenser to dispense a reagent to a container held by a holding section on the single row that is positioned at another of the at least two predetermined rest coordinate positions at which a reagent is dispensed into a reaction container held by a holding section, which is a rest coordinate position different from the rest coordinate position that a holding section holding a container is positioned to dispense a reagent during the normal analysis, and
wherein during the interrupt analysis, the computer is programmed to control the sample dispenser to dispense a sample to a container held by a holding section on the single row that is positioned at another of the at least two predetermined rest coordinate positions at which a sample is dispensed into a reaction container held by a holding section, which is a rest coordinate position different from the rest coordinate position that a holding section holding a container is positioned to dispense a sample during the normal analysis.

7. An analyzer comprising:
a disk, rotatably driven by a driving mechanism, having a plurality of holding sections on a circumference of the disk for removably holding a plurality of containers that hold a reaction solution, the driving mechanism is configured to move the plurality of containers held in the holding sections to a plurality of rest coordinate positions, which are each fixed at different angles around a circumference of the disk and do not move with the disk, and the holding sections are arranged exclusively in a single row on the circumference disk, the plurality of rest coordinate positions include at least two predetermined rest coordinate positions at which the holding section accepts a new container;
a reagent dispenser configured to dispense a reagent into the containers on the disk at one of the plurality of rest coordinate positions;
a sample dispenser configured to dispense a sample into the containers on the disk at another of the plurality of rest coordinate positions;
a measurement unit configured to measure a reaction solution in a container at yet another of the plurality of rest coordinate positions;
a magazine configured to hold a plurality of new containers;
a container transfer mechanism configured to access a plurality of holding sections and to transfer a new container from the magazine to a holding section on the single row that is positioned at any of the at least two predetermined rest coordinate positions at which the holding section accepts a new container;
a temporary container holding section disposed outside of the disk for temporarily holding one of the containers; and
a computer connected to each of the driving mechanism and container transfer mechanism,
wherein the computer is programmed to:
control the container transfer mechanism to transfer one of the containers between the disk and the temporary container holding section,
control the driving mechanism to rotate the disk according to a sequence during a normal analysis of a first reaction solution having a first reaction time, and to rotate the disk according to the sequence during an interrupt analysis of a second reaction solution having a second reaction time shorter than the first reaction time,
receive a measurement request requesting the interrupt analysis of the second reaction solution having the second reaction time that is shorter than the first reaction time,
determine whether the disk has an empty holding section which defines a state in which a new container can be supplied to a holding section on the single row that is positioned at one of the at least two predetermined rest coordinate positions at which the holding section accepts a new container, and
wherein the computer is programmed to control the container transfer mechanism according to the normal analysis and begin controlling the container transfer mechanism according to the interrupt analysis upon reception of the measurement request, upon the disk being in the state in which a new container can be supplied to a holding section on the single row that is positioned at one of the at least two predetermined rest coordinate positions at which the holding section accepts a new container,
wherein during the normal analysis, the computer is programmed to control the container transfer mechanism to transfer a new container from the magazine to a holding section on the single row that is positioned at one of the at least two predetermined rest coordinate positions at which the holding section accepts a new container, and
wherein during the interrupt analysis, the computer is programmed to control the container transfer mechanism to transfer a new container from the magazine to a holding section on the single row that is positioned at another of the at least two predetermined rest coordinate positions at which the holding section accepts a new container, which is a rest coordinate position different from the rest coordinate position that a holding section is positioned to transfer a new container during the normal analysis.

8. The analyzer according to claim 4, further comprising:
a stirring mechanism for stirring the sample and the reagent in one of the containers prior to measuring,
wherein the container transfer mechanism transfers one of the containers from one of the holding sections of the disk at a first rest coordinate position to the stirring mechanism.

9. The analyzer according to claim 8,
wherein the stirring mechanism stirs the sample and the reagent in the one of the containers transferred by the container transfer mechanism, and
the container transfer mechanism transfers the one of the containers from the stirring mechanism to another one of the holding sections of the disk at a second rest coordinate position.

10. The analyzer according to claim 7, wherein
the plurality of rest coordinate positions include at least two predetermined rest coordinate positions at which a reagent is dispensed into a reaction container held by a holding section,
wherein the plurality of rest coordinate positions include at least two predetermined rest coordinate positions at which a sample is dispensed into a reaction container held by a holding section,
wherein during the normal analysis, the computer is programmed to control the reagent dispenser to dispense a reagent to a container held by a holding section on the single row that is positioned at one of the at least two predetermined rest coordinate positions at which a reagent is dispensed into a reaction container held by a holding section,
wherein during the normal analysis, the computer is programmed to control the sample dispenser to dispense a sample to a container held by a holding section on the single row that is positioned at one of the at least two predetermined rest coordinate positions at which a sample is dispensed into a reaction container held by a holding section,
wherein during the interrupt analysis, the computer is programmed to control the reagent dispenser to dispense a reagent to a container held by a holding section on the single row that is positioned at another of the at least two predetermined rest coordinate positions at which a reagent is dispensed into a reaction container held by a holding section, which is a rest coordinate position different from the rest coordinate position that a holding section holding a container is positioned to dispense a reagent during the normal analysis, and
wherein during the interrupt analysis, the computer is programmed to control the sample dispenser to dispense a sample to a container held by a holding section on the single row that is positioned at another of the at least two predetermined rest coordinate positions at which a sample is dispensed into a reaction container held by a holding section, which is a rest coordinate position different from the rest coordinate position that a holding section holding a container is positioned to dispense a sample during the normal analysis.

11. An analyzer comprising:
a disk, driven by a driving mechanism, having a plurality of holding sections on a circumference of the disk for removably holding a plurality of containers, the driving mechanism is configured to move the plurality of containers held in the holding sections to a plurality of rest coordinate positions, which are each fixed at different angles around a circumference of the disk and do not move with the disk, and the holding sections are arranged exclusively in a single row on the circumference disk;
a reagent dispenser configured to dispense a reagent into the containers on the disk at one of the plurality of rest coordinate positions;
a sample dispenser configured to dispense a sample into the containers on the disk at another of the plurality of rest coordinate positions;
a stirrer disposed outside of the disk and configured to stir a reaction solution;
a measurement unit configured to measure a reaction solution in a container at yet another of the plurality of rest coordinate positions;
a magazine configured to hold a plurality of new containers;
a container transfer mechanism configured to access a plurality of holding sections and to transfer a new container from the magazine to a holding section on the single row that is positioned at a rest coordinate position at which the holding section accepts a new container, and configured to transfer a container having a reaction solution between a holding section positioned at a rest stop coordinate and the stirrer; and
a computer connected to each of the driving mechanism, reagent dispenser, sample dispenser, measurement unit, stirrer, and container transfer mechanism,
wherein the computer is programmed to:
control the driving mechanism to rotate the disk according to a sequence during a normal analysis of a first reaction solution having a first reaction time, and to rotate the disk according to the sequence during an interrupt analysis of a second reaction solution having a second reaction time shorter than the first reaction time,
receive a measurement request requesting the interrupt analysis of the reaction solution having the second reaction time that is shorter than the first reaction time,
wherein the computer is programmed to control the container transfer mechanism according to the normal analysis and begin controlling the container transfer mechanism according to the interrupt analysis upon reception of the measurement request,
wherein during the normal analysis, the computer is programmed to control the container transfer mechanism to transfer a container from the stirrer to a holding section on the single row that is positioned at one of at least two predetermined rest coordinate positions at which the holding section accepts a container being returned from the stirrer, and
wherein during the interrupt analysis, the computer programmed to control the container transfer mechanism to transfer a container from the stirrer to a holding section on the single row that is positioned at another of the at least two predetermined rest coordinate positions at which the holding section accepts a container being returned from the stirrer, which is a rest coordinate position different from the rest coordinate position that a holding section is positioned to transfer a container from the stirrer during the normal analysis.

* * * * *